United States Patent [19]

Weber, Jr. et al.

[11] Patent Number: 5,035,695
[45] Date of Patent: * Jul. 30, 1991

[54] EXTENDABLE ELECTROCAUTERY SURGERY APPARATUS AND METHOD

[75] Inventors: Jaroy Weber, Jr., 2630 Bear Gulch Rd., Woodside, Calif. 94062; Terrance L. Kloeckl, San Francisco, Calif.; Michael A. Kast, Palo Alto, Calif.; Frank T. Watkins, III, Menlo Park, Calif.

[73] Assignee: Jaroy Weber, Jr., Woodside, Calif.

[*] Notice: The portion of the term of this patent subsequent to Apr. 24, 2007 has been disclaimed.

[21] Appl. No.: 491,568

[22] Filed: Mar. 9, 1990

Related U.S. Application Data

[62] Division of Ser. No. 125,652, Nov. 30, 1987, Pat. No. 4,919,129.

[51] Int. Cl.$^5$ ............................................. A61B 17/39
[52] U.S. Cl. ...................................... 606/42; 604/35; 606/45; 606/49
[58] Field of Search ...................... 606/42, 45, 46, 48, 606/49, 50; 128/800, 801; 604/35

[56] References Cited

U.S. PATENT DOCUMENTS

| | | | |
|---|---|---|---|
| 1,750,874 | 3/1930 | Campbell | 606/42 |
| 1,978,495 | 10/1934 | Landau | 606/45 |
| 4,307,720 | 12/1981 | Weber, Jr. | 606/49 |
| 4,311,145 | 1/1982 | Esty et al. | 606/42 |
| 4,919,129 | 4/1990 | Weber, Jr. et al. | 606/42 |

*Primary Examiner*—Lee S. Cohen
*Attorney, Agent, or Firm*—A. C. Smith

[57] ABSTRACT

An improved electrocautery method and instrument includes interlock features which enable the instrument to be safely operated under convenient manual controls including a slide element and control buttons and interlock switch positioned on the instrument.

4 Claims, 5 Drawing Sheets

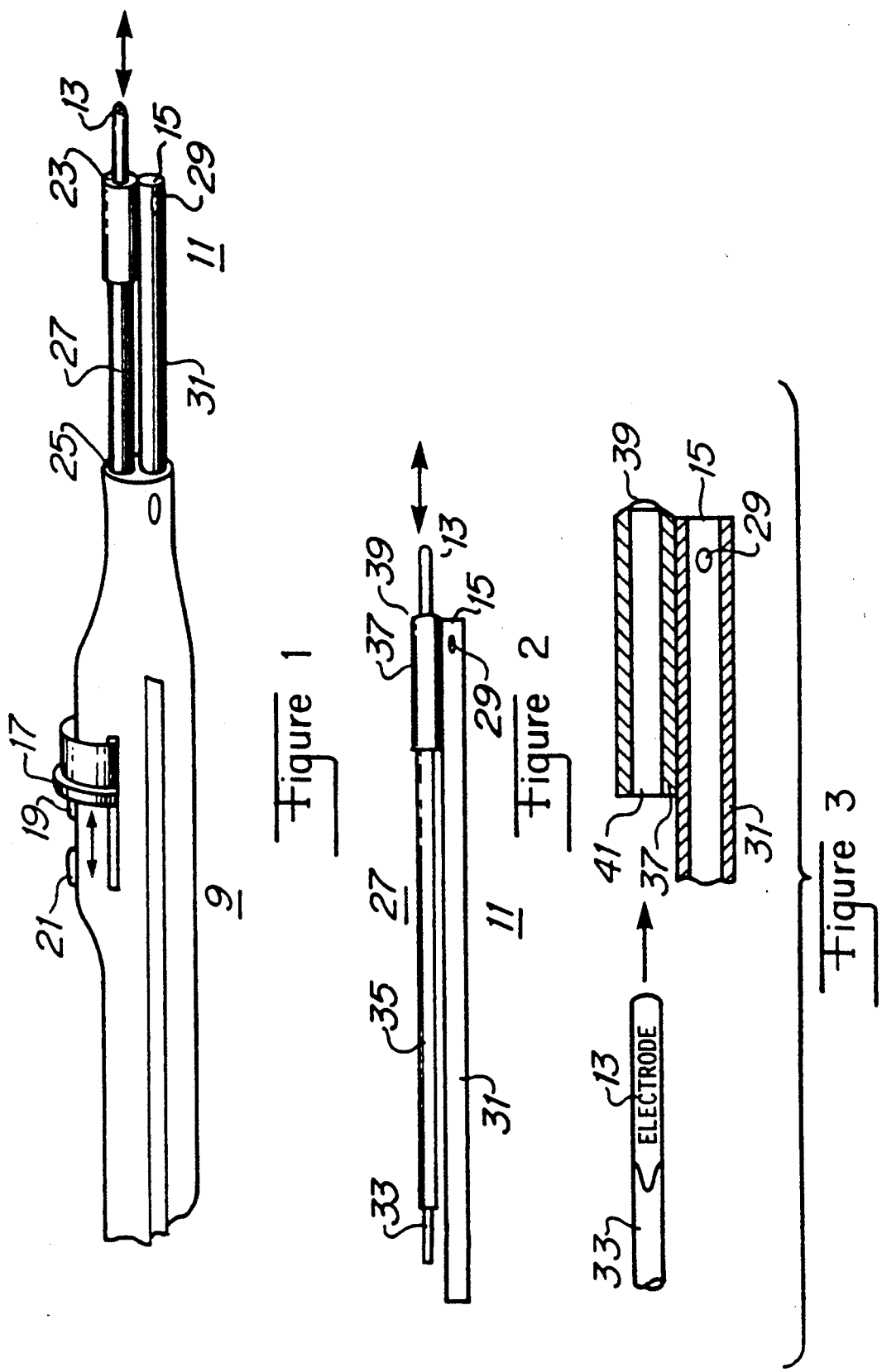

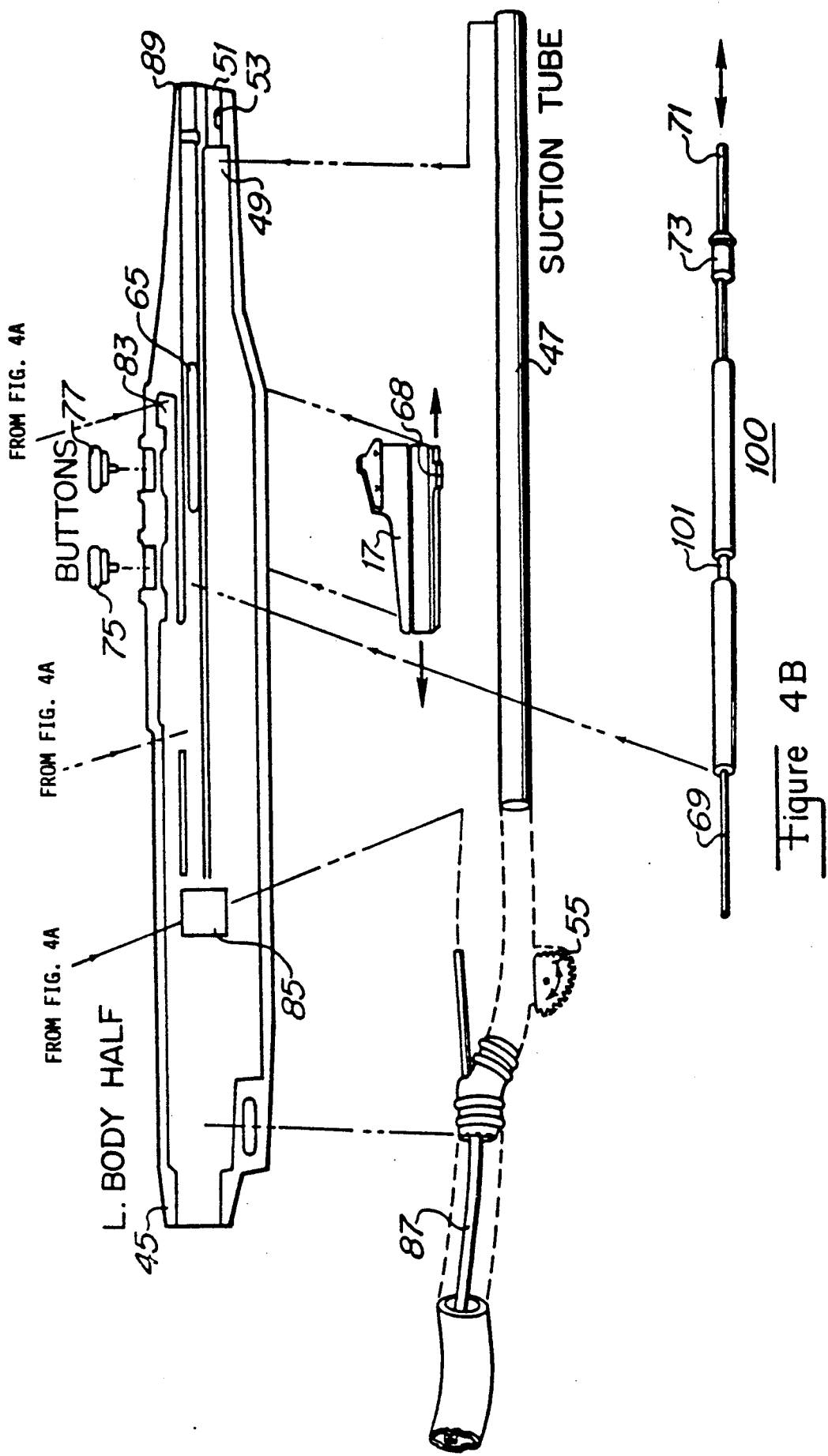

EXTENDABLE ELECTROCAUTERY SURGERY APPARATUS AND METHOD

This is a divisional of copending application Ser. No. 07/125,652 filed on Nov. 30, 1987, now U.S. Pat. No. 4,919,129.

RELATED CASE

The subject matter of this application is related to the subject matter of U.S. Pat. No. 4,307,720 which is incorporated herein by reference.

BACKGROUND OF THE INVENTION

Field of Invention

This invention relates to electrocautery surgical instruments and more particularly to an electrocautery scalpel system having variably extendable suction and electrode elements to facilitate electrocautery surgery at deep locations within surrounding tissue.

Electrocautery instruments commonly rely upon high-voltage, high-frequency electrical signals of various waveforms to selectively sever, clamp or coagulate living tissue during surgical procedures. In addition, many such electrocautery instruments include integral vacuum conduits and associated suction apparatus for evacuating tissue fluids and volatized tissue materials that commonly accompany electrocautery incision of living tissue. Devices of these types are disclosed in the literature (see, for example, U.S. Pat. Nos. 1,311,494; 1,963,636; 2,002,594; 2,894,512; 3,662,151; 3,682,162; 3,828,780; 3,835,842; 3,850,175; 3,884,237; 3,902,494; 3,906,955; 3,974,833; 3,987,795; 4,011,872; 4,112,950; and 4,562,838; and French Patent No. 73.30854). Electrocautery instruments of these types also commonly employ a retractable electrode or a vacuum port to enhance the utility of the instrument during surgical procedures. One difficulty encountered with certain electrocautery scalpels having extendable and retractable electrodes is that the geometry of the instruments usually limits the depth in tissue to which the instruments can conveniently penetrate without expanding the incision to accommodate the surgeon's hand. As certain surgical procedures progress and penetrate deeper into a surgical site, it is frequently desirable to extend the instrument to longer dimension with control over the retractable electrode in order to facilitate advancing the surgery into deep, confined sites.

SUMMARY OF THE INVENTION

In accordance with the present invention, an improved electrocautery surgical instrument includes a retractable electrode and a vacuum conduit for selectively evacuating a surgical site, and also includes attachable extension units of various lengths for selectively extending the operational utility of the instrument as a surgical procedure progresses. The vacuum port and slidable electrode/blade of the instrument are thereby extended a selected dimension to facilitate deep surgical procedures in confined sites. Safety switching is included within the instrument to control application of high-voltage electrical signals to the electrode/blade and to permit the user to establish electrically inactive conditions during attachment and removal of extension units. The electrocautery surgical instrument thus configured according to the present invention facilitates surgical procedures in deep surgical sites as well as in shallow surgical sites without having to replace the instrument in the surgeon's hand during the surgical procedure.

DESCRIPTION OF THE DRAWINGS

FIG. 1 is a partial perspective view of the electrocautery surgical instrument with an attached extension unit; and FIG. 2 is a side view of the extension unit of FIG. 1; and FIG. 3 is a partial sectional assembly view of the extension unit of FIG. 1; and FIG. 4, 4(A) and 4(B) are an exploded assembly view of the instrument of FIG. 1.

DESCRIPTION OF THE PREFERRED EMBODIMENT

Figures 4, 4A:
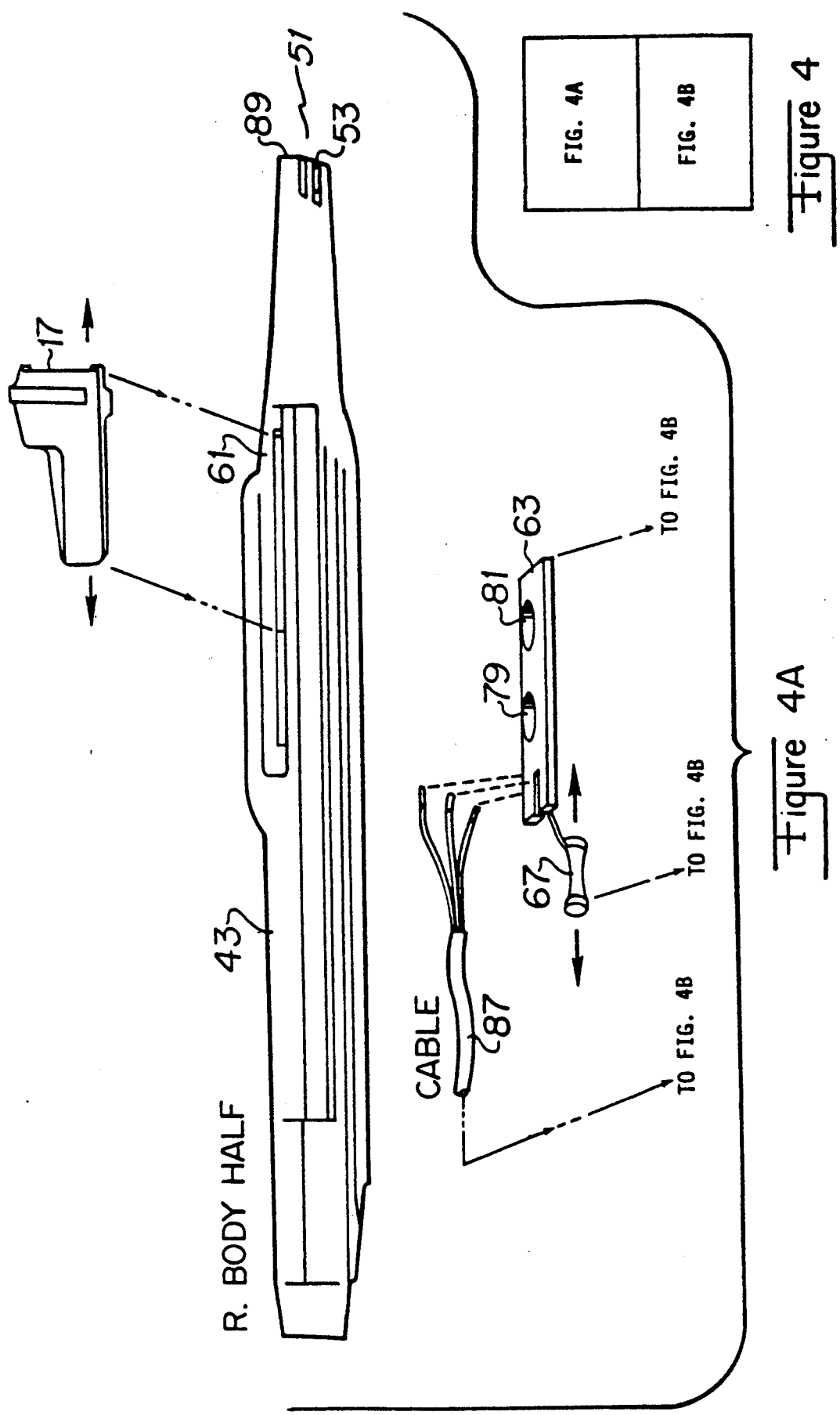

Referring now to FIG. 1, there is shown a perspective view of the electrocautery instrument 9 with an extension unit 11 attached to the front end of the instrument. Specifically, the retractable electrode/blade 13 is extended forward and is retractable within the extension unit 11, and the vacuum port 15 is also extended forward from the instrument 9 to provide substantially the same blade 13 and port 15 characteristic at the front of the extension unit 11 as are available on the front of the instrument 9 without the extension unit 11 in place. The extension units 11 may be of variable length as desired to facilitate deep surgical procedures, and may be attached and removed as desired by press-fit or snap-toggle attachment on the front of the instrument 9. A manually-slidable element 17 is attached to the electrode 13 to control the extent of the protrusion of the electrode 13 from the front of the attached extension unit 11. Push buttons 19 and 21 are provided to control application of different high-voltage, high-frequency waveforms to the electrode 13 for either incising or cauterizing tissue in known manner. In addition, the guide opening for the electrode 13 at the front of the extension unit 11 may be disposed closely about the blade 13 to scrape off adherent coagulum and tissue materials as the electrode is retracted therethrough in response to manual activation of the slide element 17. The Portion 27 of electrode 13 that is exposed is insulated to facilitate manipulation of the instrument within surrounding tissue without undesirably discharging electrical signals to surrounding tissue in the region 27 between the electrode 13 and the front 25 of the unit 9. A decompression port 29 is disposed in at least one lateral dimension from the vacuum port 15 to control the maximum pressure differential that can be developed at the vacuum port 15 under conditions of the port 15 being occluded by tissue which might be damaged by excessive suction.

Referring now to FIG. 2, there is shown a side view of the extension unit 11. The lower tube 31 is the vacuum conduit with the vacuum port 15 and decompression port 29. The upper electrode 13 and connecting conductor 33 is insulated 35 over the region 27 that extends between the instrument 9 and the exposed electrode 13. The body 37 of the extension unit 11 may be welded, glued or otherwise attached to the vacuum tube 31, and serves as a guide for the electrode 13 which is slideably mounted therein. The electrode 13 may be needle-like, or generally flat (i.e., its width is greater than the thickness) to serve as a surgical blade. The body 37 may include a scraping guide 39 for removing adherent coagulum and tissue material as the electrode 13 and the conductor 33 to which it is attached is withdrawn into and through the body 37.

The sectional view of FIG. 3 illustrates the attachment of the vacuum tube 31 to the body 37. Also, the electrode/blade 13 portion of the conductor 33 is shown disposed to slide within the guide way 41 in the body 37 through and past the scraping means 39 at the forward end thereof. Alternative embodiments of scraping means are described herein with reference to FIGS. 7 and 8.

Referring now to the exploded assembly drawing of FIG. 4, there is shown the internal features of the instrument 9 which accommodate attachment of the extension unit 11 on the front end thereof. Specifically, the right and left half sections 43, 45 of the instrument 9 are disposed to house the switches, electrode, manual slider, vacuum conduit and valving, and associated wiring to form the electrocautery instrument when assembled as shown. The vacuum conduit or suction tube 47 in the lower portion of the sections 43,45 is positioned in fluid-tight engagement 49 with the vacuum port 51 in the forward end of the instrument 9, which vacuum port has an inner diameter (or other cross-sectional dimensions) that receive therein the attachment end of the vacuum conduit 31 of the extension unit 11 in press-fitted, fluid-tight engagement. Alternatively, jam taper fit, or threaded engagement, or snap-fitting o-ring on an annular recess may be used to seal and secure the instrument and extension unit together as well as form a continuation of the vacuum conduit 47, 31. Also, the vacuum port 51 of the instrument 9 may have a decompression port 53 for limiting the pressure differential at the port, as previously described with reference to the ports 15, 29 on the extension unit 11. This decompression port 53 is disposed within a socket or receptacle of the vacuum port 51 to be sealed off by insertion into such socket or receptacle of the connecting end of the vacuum conduit 31 of the extension unit 11. The vacuum conduit is therefore extended forward to the vacuum and decompression ports 15, 29 of the extension unit 11 when the extension unit 11 is properly attached to the front of the instrument 9. This vacuum conduit may be connected via a suitable control valve such as a roller 55 disposed to manually Pinch off the flexible conduit 47 that connects to a remote vacuum supply (not shown). In this way, the operating surgeon may control the application of suction at a surgical site by positioning the vacuum port 15 (or 51, if an extension unit 11 is not attached) and by manually rotating the pinch roller 55 to selectively pinch off the flexible conduit 47, and thereby control the vacuum action at the port 15.

In the upper portion of the instrument 9, the slide element 17 is disPosed to slide longitudinally in tracks or grooves 61 in the body of the instrument 9. The tab 68 that protrudes from the slide element 17 through a groove 65 engages the slide electrode 100 at the recess 101 to thereby control retraction and extension of the electrode 71 under manual control of the slide element 17. The electrode conductor 69, in one embodiment of the present invention, may slide in electrical contact through contactor 67 to engage the safety switch 85 in its rearward-most retracted position. The electrode 71 attaches 73 to the slide electrode 100 at the forward end thereof for gripping the electrode/blade 71 (or the contact end 33 of the electrode conductor 35 of an extension unit 11) by friction or snap-toggle engagement, or the like, in known manner. The switch plate 63 includes conventional dome-type switches 79, 81 which may be activated by the push buttons 75, 77 that are mounted in the body of the instrument 9. Thus, the push-button switches 79, 81 may be manually activated when the slide element 17 (and therefore the electrode/blade 71 or 13) is positioned in the forward location. In the rearward position of the slide element 17, one or more of the push-button switches 79, 81 are shrouded by the slide element 17 as protection against inadvertent manual activation. Additionally, the rearward end of the electrode conductor 69, 71, is disposed to engage an interlock switch 85 that is wired into the circuit including the electrode and a source (not shown) of high-frequency, high-voltage electrical signals. Thus, electrical signals for either severing or cauterizing tissue are connected from such source via a cable 87 (which may be integral with the vacuum conduit for convenience) to the switches 79, 81 on the switch plate 63. The interlock switch 85 is thus disposed to cut off the application of all electrical signals when the electrode conductor 69 is in the rearward-most position. In this position, the slide element 17 shrouds either or both of the Push buttons 75, 77 as a further safety interlock feature while the electrode is withdrawn rearwardly into the body of the instrument 9 (or into the body 37 of an extension unit 11). Scraping means 89, as illustrated in FIG. 7, may be disposed about the electrode/blade 71 to dislodge adherent coagulum and tissue material as the electrode/blade 71 is withdrawn into the body under manual control of the slide element 17. Thus, during operating procedures, the electrode/blade 71 (or 13 of an extension unit 11) may be withdrawn into the body of the instrument 9 (or of the extension unit 11) under manual control of the slide element 17 to clean the blade and to configure the front end of the unit to facilitate its use simply as a vacuum probe to evacuate a surgical site. In this configuration, the push buttons 75, 77 are shrouded against inadvertent activation, and the roller 55 may be manually activated to pinch and unpinch the flexible tubing 47, as desired. Alternatively, the electrode 71 (or 13 of an extension unit 11) may be advanced under manual control of the slide element 17 to protrude from the instrument 9 (or extension unit 11). In this configuration, the push buttons 75, 77 are exposed and may be manually activated to control the supply of either severing or coagulating electrical signals to the electrode/blade via the interlock switch 85.

Figure 5:
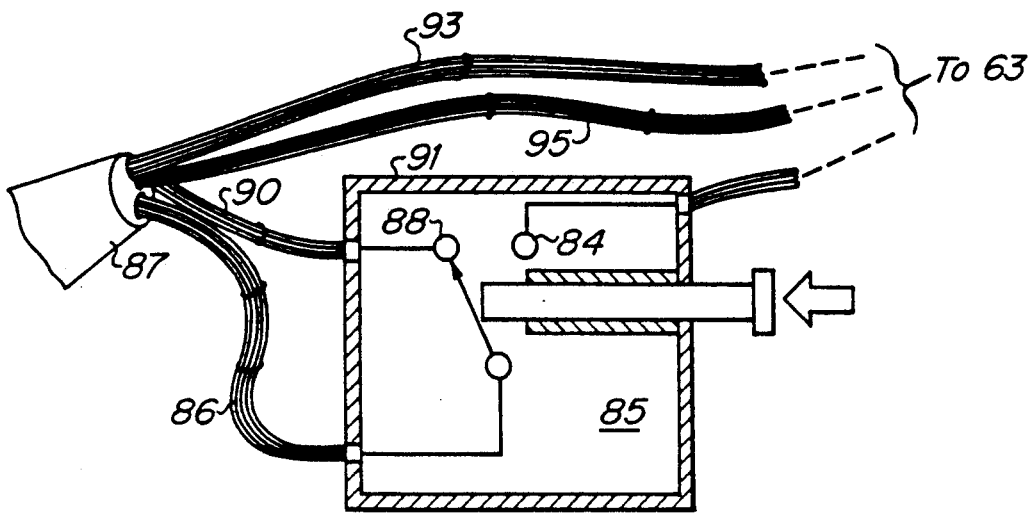
FIG. 5 is a sectional view of the interlock switch of FIG. 4.

Referring now to FIG. 5, there is shown a sectional view of one embodiment of the interlock switch 85 which is disposed within an enclosing housing 91 to be actuated by the rearward end of the electrode conductor 69. Thus, the control leads 93, 95 (which may conduct low-voltage control signals) from the push button switches 79, 81 on the contact plate 63 connect via the cable 87 to a conventional source (not shown) of high-voltage, high-frequency signal, and such signal is thus supplied through a power conductor 86 in the cable 87 and through contact 84 of the interlock switch 85 to the switch plate 63, slide contactor 67, and electrode 71 (or 13). In the rearward-most or retracted position of the electrode conductor 69, the power conductor 86 may be shunted to ground through alternate contact 88 and a ground conductor 90 in the cable 87.

Figure 6:
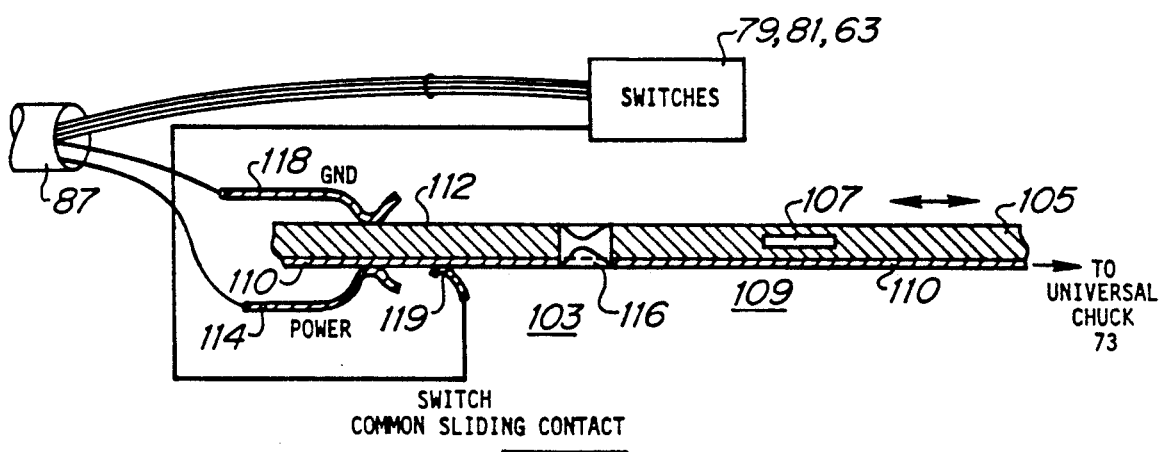
FIG. 6 is a sectional view of another embodiment of the interlock switch according to the present invention.

In another embodiment of the interlock switch 85 according to the present invention, as illustrated in the sectional view of FIG. 6, the electrode conductor 69 of FIG. 4 is formed in a printed-circuit like structure 103 including a non conductive central region 105 having a recess 107 to receive the tab 68 of the slide element 17, and a rearward section 109 that includes a conductor 110 disposed on an insulating layer 112. The conductor 110, of course, connects to the attaching means (or universal chuck) 73, and is slideably engaged by contacts 114 and 119. Electrical signal on contacts 114 (from a signal generator not shown) is applied to the electrode 71 (or 13 of an extender unit) while such electrode is in extended position under the manual control of the slide element 17. However, the insulating layer 112 of the electrode conductor 69 includes an aperture 116 at a location approximately at the maximum rearward extent of travel (i.e. retracted electrode) and in line with the contact 114. Another sliding contact 118 is disposed to connect to the contact 114 only within the aperture 116, and to be insulated therefrom by the insulating layer 112 otherwise. In the retracted position of structure 103, the sliding contact 119 may also be insulated by 112 from conductor 110 based upon the particular pattern of the conductor 110. Contact 118 may be connected back to ground via the shield on cable 87. Therefore, the electrode 13 or 71 may be effectively grounded while in the retracted position to prevent inadvertent electrical excitation of the electrode blade 71 (or 13) during configuration and use of the instrument as a vacuum probe, or during attachment of detachment of an extension unit.

Figure 7A:
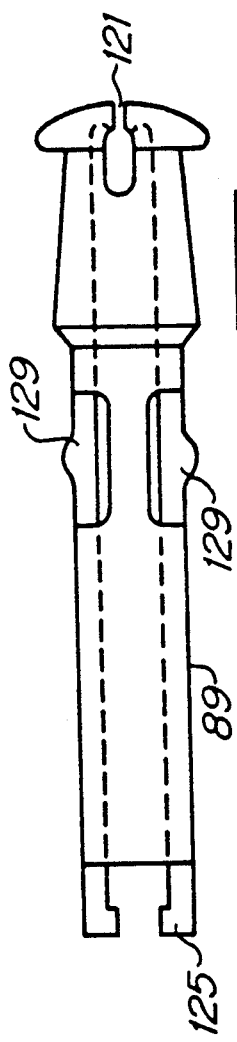
FIG. 7(A) and (B) are plan and sectional views, respectively, of the body of the electrode scraping means.
Figure 7B:
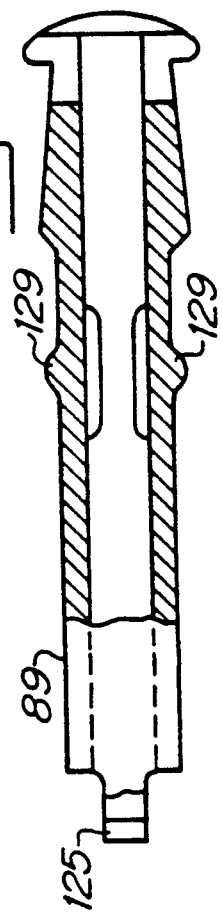
Figure 8A:
FIGS. 8(A) and (B) are plan and side views, respectively, of a flat, blade-like electrode for assembly within the body of FIG. 7.
Figure 8B:
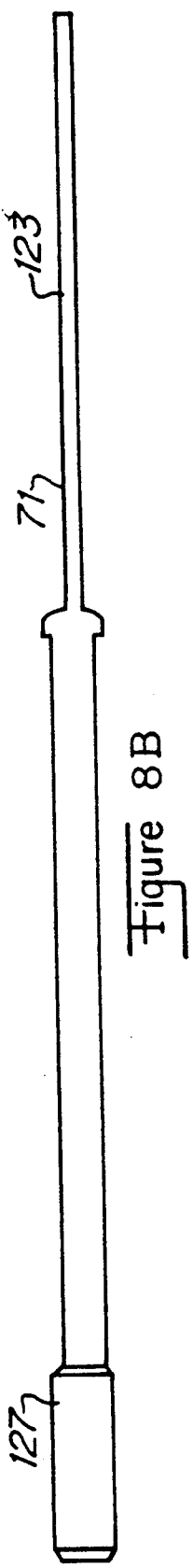

Referring now to FIG. 7A and B, there are shown plan and sectional views, respectively, of the scraping means 89 for guiding and scraping the electrode blade illustrated in FIGS. 8A and B. Specifically, these views illustrate the ferrule-like structure 89 of FIG. 7 that may conveniently snap into place near the forward edge of the instrument (or of an extension unit) for easy replacement of electrodes of different configurations (e.g. flat or needle-like). Thus, the scraping means 89 includes a generally hollow body through which the electrode 13 of FIG. 8 slides, and includes a close-fitting forward aperture 121 which engages the blade portion 123 of the electrode 13 is sliding, contacting relationship. The rear portion of the body 89 includes resilient jaws-like structure 125 to facilitate assembly of the electrode 71 (including the section 127 of expanded diameter) into the body from the rearward end toward the forward end. The jaws-like structure return to position to retain the electrode 71 entirely to captivated and slideable within the body 89. The section 127 is received by and retained in the attachment means 73 to facilitate the mechanical sliding motion of the electrode 71 within the body 89 under manual control of the user. Spring-like protrusions 129 formed on the body 89 about its central section facilitate the snap-in retention of the body 89 and captivated electrode 71 within and near the forward end of the instrument 9. Thus, electrodes 71 of different shapes and lengths may be conveniently inserted in and removed from the instrument (or extension units) as the surgical operation proceeds.

In operation, the instrument 9 (with or without attached extension unit 11) may be configured to operate either as a vacuum probe alone (with the electrode/blade 71, 13 retracted) or as an electrosurgical instrument with the electrode/blade 13, 71 extended into operational position. In the latter configuration, the electrical control buttons are exposed and the safety, interlocking switch is actuated to permit high-voltage, high-frequency electrical signals to be supplied to the protruding electrode/blade under control of one or more of the uncovered, exposed push buttons. The operational length of the instrument may be altered by attaching or detaching extension units of desired length. The vacuum port of the instrument is altered by attachment of an extension unit, and the electrode/blade of the extension unit is electrically connected and mechanically attached for convenient manual extension and retraction control from the instrument.

Therefore, the method and apparatus of the present invention facilitates the convenient extension of an electrocautery surgical instrument to accommodate surgical procedures performed deep within surrounding tissue while providing interlock features that enhance the safety and utility of the instrument during attachment and detachment of extension units and during its operation as a vacuum probe.

I claim:

1. Surgical apparatus comprising:
   an elongated body having a forward end and a rearward end;
   conductor means for supplying electrical signal extending substantially through the body from near the rearward end to near the forward end thereof;
   means within the body slidably supporting the conductor means for selective slideable positioning thereof between rearward-most and forward-most positions along a slideable path relative to said forward end;
   slider means slideably disposed on the body and coupled to the conductor means for selectively altering the position thereof along the slideable path relative to said forward end; and
   circuit mean including the conductor means for controlling the application of electrical signal thereto in response to the position of the conductor means along the slideable path thereof;
   said circuit means including an interlock switch means operable in conductive state and in non-conductive state and disposed to be actuated for operation in the non-conductive state in response to the conductor means being positioned near a rearward-most position along the slideable path thereof, and in the conductive state in response to the conductor means being positioned near a forward-most along the slideable path thereof, said interlock switch means including auxiliary switch means disposed in the body for grounding the conductor means during operation in said non-conductive state.

2. Surgical apparatus comprising:
   an elongated body having a forward end and a rearward end;
   conductor means for supplying electrical signal extending substantially through the body toward the forward end thereof;
   means with the body slideable supporting the conductor means for selective slideable positioning thereof between rearward-most and forward-most positions along a slideable path relative to said forward end;

slider means slideably disposed on the body and coupled to the conductor means for selectively altering the position thereof along the slideable path relative to said forward end; and circuit means including the conductor means for controlling the application of electrical signal thereto in response to the position of the conductor means along the slideable path thereof;

said circuit means including an interlock switch means operable in conductive state and in non-conductive state and disposed to be actuated for operation in the non-conductive state in response to the conductor means being positioned near a rearward-most position along the slideable path thereof, and in the conductive state in response to the conductor means being positioned near a forward-most position along the slideable path thereof;

switch means including at least one switch mounted in the body and including an actuator therefor positioned on the body for manually actuating said one switch for selectively applying electrical signal through said circuit means to the conductor means; and a slide element disposed on the body and coupled to the conductor means for manually positioning the same along the slideable path thereof;

said slide element including means oriented to shroud the actuator against manual operation thereof in response to the conductor means and the slide element coupled thereto being disposed near the rearward position along the slideable path thereof.

3. A method of operating an electrosurgical instrument including a manually-controlled slideable electrical conductor extendable from a forward end of the instrument to controllable supply suitable electrical signal for treating tissue, the method comprising the steps of:

slideably supporting the electrical conductor within the instrument for longitudinal sliding motion between a forward position for which the electrical conductor extends from the forward end of the instrument, to a rearward position for which the electrical conductor is substantially retracted within the forward end of the instrument for selectively manually extending and retracting the electrical conductor relative to said forward end in response to manual control of the slideable position of the electrical conductor within the instrument; and inhibiting the application of electrical signal including grounding the electrical conductor in response to the positioning of the electrical conductor near the rearward slideable position thereof.

4. The method of operating an electrosurgical instrument according to claim 3 in which a switch and a manual actuator therefor is mounted on the instrument and a slide element is disposed on the instrument for manually positioning the electrical conductor, the method comprising the step of:

coupling the switch to selectively supply electrical signal to the electrical conductor suitable for treating tissue in response to manual actuation of the actuator for the switch; and positioning the slide element for shrouding the actuator against manual actuation thereof in response to the electrical conductor being positioned near the rearward position thereof.

* * * * *